(12) United States Patent
Gil et al.

(10) Patent No.: US 8,216,245 B2
(45) Date of Patent: Jul. 10, 2012

(54) APPARATUS AND METHOD FOR APPLYING SUSTAINED TENSION ON A TETHER

(75) Inventors: Carlos E. Gil, Collerville, TN (US); Aleksandr G. Zolotov, Collierville, TN (US); Jason M. May, Cordova, TN (US)

(73) Assignee: Warsaw Orthopedic, Warsaw, IN (US)

( * ) Notice: Subject to any disclaimer, the term of this patent is extended or adjusted under 35 U.S.C. 154(b) by 260 days.

(21) Appl. No.: 12/609,453

(22) Filed: Oct. 30, 2009

(65) Prior Publication Data

US 2011/0106185 A1 May 5, 2011

(51) Int. Cl.
*A61B 17/58* (2006.01)
(52) U.S. Cl. ........................................ 606/103
(58) Field of Classification Search .................. 606/144, 606/148, 254, 255, 256, 258, 261, 262, 99, 606/86 R, 86 A, 74, 103, 101, 104, 279; 600/225, 600/229
See application file for complete search history.

(56) References Cited

U.S. PATENT DOCUMENTS

| | | | |
|---|---|---|---|
| 5,431,659 A | * | 7/1995 | Ross et al. .................. 606/103 |
| 5,935,133 A | | 8/1999 | Wagner et al. |
| 2009/0054902 A1 | | 2/2009 | Mickiewicz et al. |

* cited by examiner

*Primary Examiner* — Kevin T Truong
*Assistant Examiner* — Diana S Jones

(57) ABSTRACT

Apparatus for applying sustained tension on tether in treatment site includes a positioning mechanism, gripping mechanism and pressurized fluid actuated mechanism. The positioning mechanism is operable to position the pressurized fluid actuated mechanism at a fixed distance relative to treatment site, and to engage a target at treatment site and secure the tether proximate to the target. The gripping mechanism is operable to selectively grip the tether and maintain tether when tether is held in tension. The pressurized fluid actuated mechanism is selectively operable to apply desired pulling force on gripping mechanism directed away from treatment site so as to transmit and apply in a sustained manner the desired pulling force on the tether independently from the tether displacement and place it under desired level of tension while the tether is being secured.

15 Claims, 12 Drawing Sheets

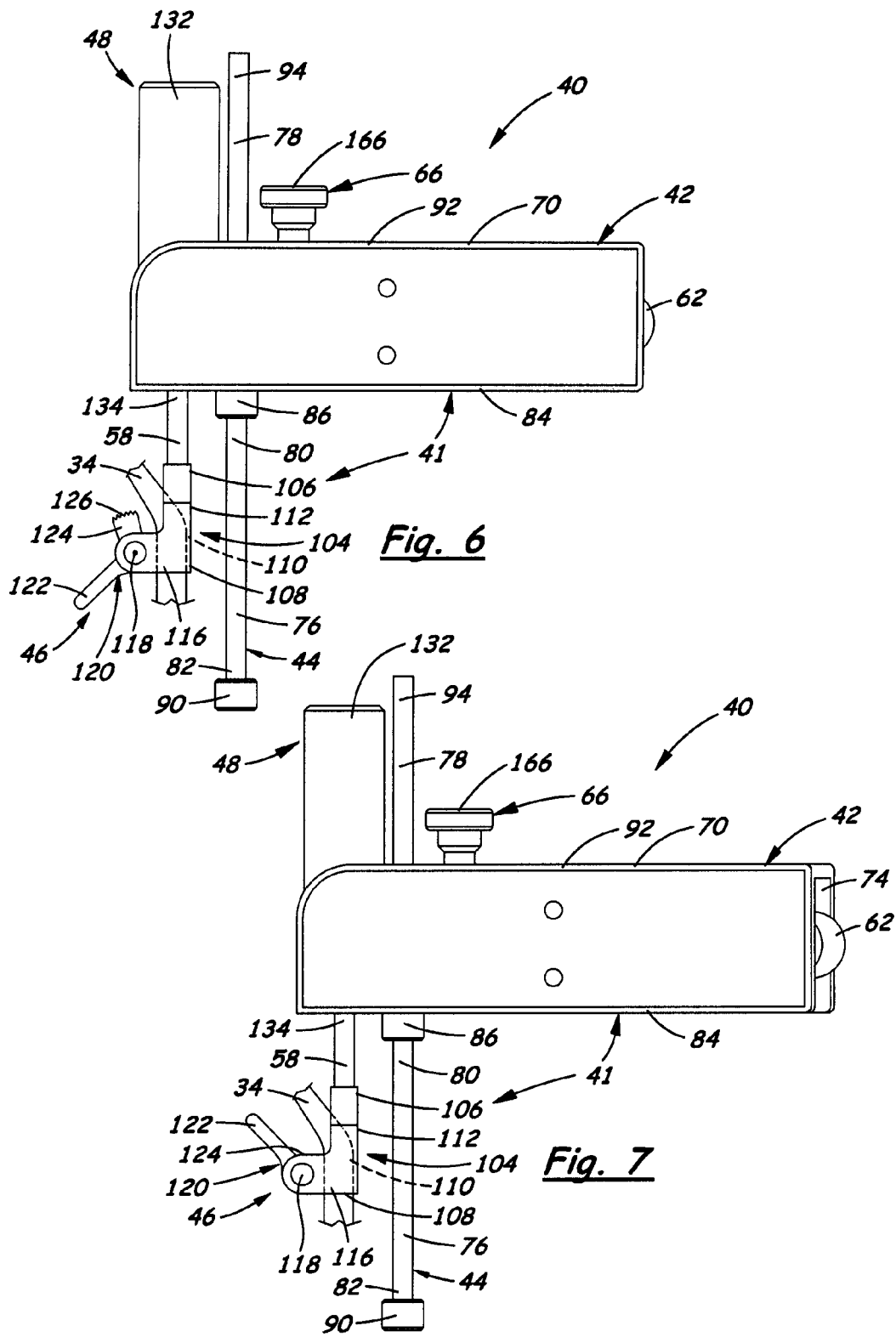

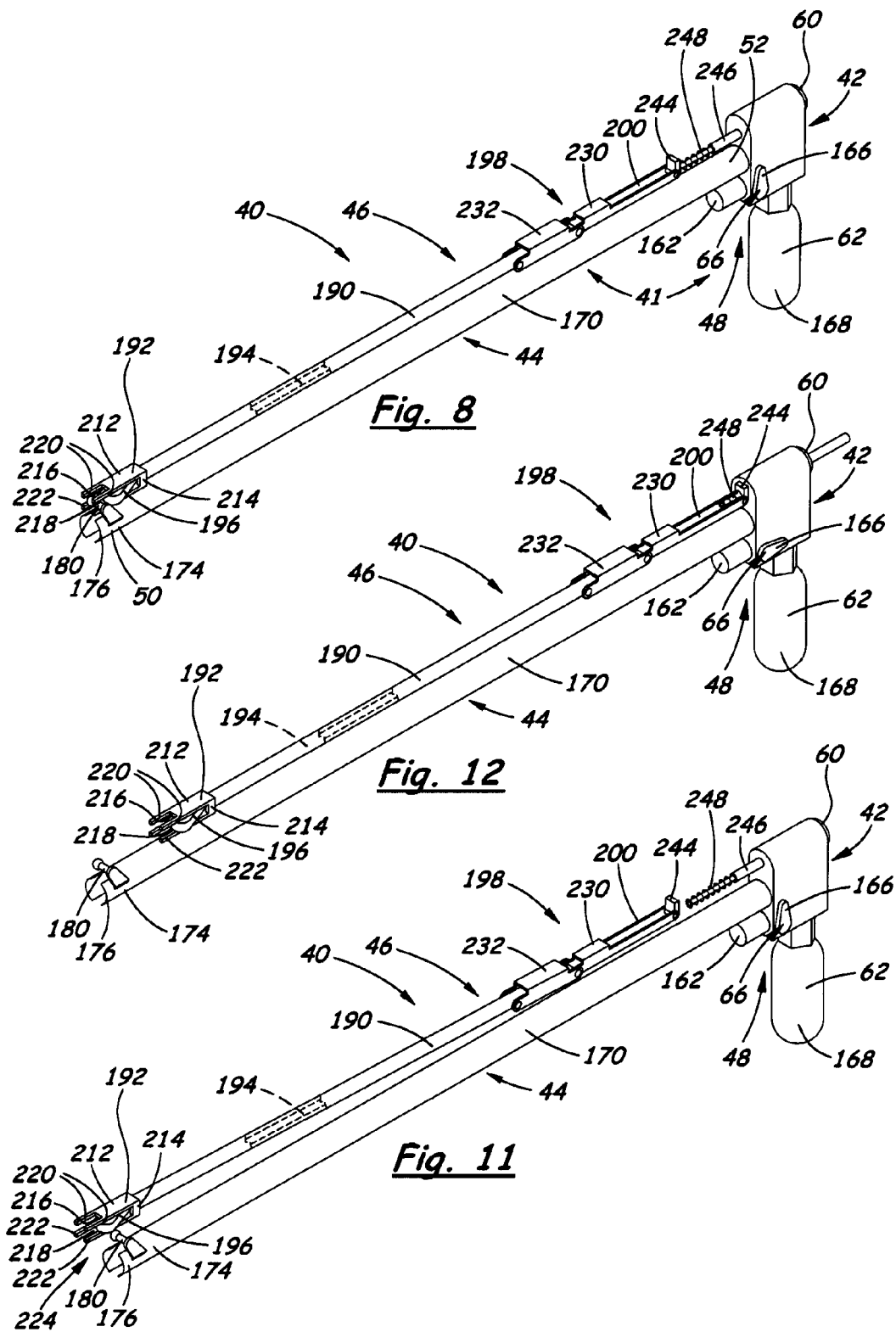

APPARATUS AND METHOD FOR APPLYING SUSTAINED TENSION ON A TETHER

BACKGROUND

1. Field of the Invention

The present invention relates generally to correction of spinal deformities and, more particularly, to an apparatus and a method for applying sustained tension on a tether used in a treatment site.

2. Description of the Related Art

Tools and methods have been developed for tensioning flexible elongate media (hereinafter generically referred to as a tether) used in various surgical applications. One such surgical application is correction of pediatric deformities. During such surgical procedure, it is required that the tether has a predetermined tension before fixing it in place. Tensioning tools, in particular, need to provide a way to impart some predetermined measurable tension on the tether and maintain this tension before the tether is fixed or constrained in some manner to a target, such as bone or an implanted anchor device, during a medical procedure in a treatment site.

However, at various times after the desired predetermined tension has been applied on the tether, the tether will elongate under the load, changing form or location, bones or implant move relatively each other and, as a result, the tension in the tether changes. The fact that this undesirable event may occur from time to time demonstrates the need for a technique and means to carry out permanent tension measurement and adjustment before and during the time when the tether is fixed or constrained.

Thus, there is still a need for an innovation that will overcome the above-described problem.

SUMMARY OF THE INVENTION

The present invention meets this need by providing an innovation that will impart accurate, permanently measurable and adjustable level of tension in a tether independently from the tether displacement.

Accordingly, in an aspect of the present invention, an apparatus for applying sustained tension on a tether in a treatment site includes a positioning mechanism, a gripping mechanism and a pressurized fluid actuated mechanism. The positioning mechanism has a distal portion operable to engage a target at the treatment site proximate to where the tether is to be secured. The positioning mechanism also has a proximal portion displaced from the distal portion. The gripping mechanism is operable to grip the tether and maintain the grip of the tether when the tether is held in tension. The pressurized fluid actuated mechanism is supported by the proximal portion of the positioning mechanism at a position a fixed distance relative to the treatment site. The pressurized fluid actuated mechanism is operable to apply a controlled tensioning force via the gripping mechanism to the tether independently from the tether displacement and thereby to place the tether under a desired level of sustained tension.

In another aspect of the present invention, an apparatus for applying sustained tension on a tether in a treatment site includes a gripping mechanism, a positioning mechanism and a pressurized fluid actuated mechanism. The gripping mechanism is operable to selectively grip and release the tether and maintain the grip of the tether when the tether is held in tension. The positioning mechanism is operable to engage a target at the treatment site proximate to where the tether is to be secured. The pressurized fluid actuated mechanism is supported by the positioning mechanism at a position a fixed distance relative to the treatment site. The pressurized fluid actuated mechanism includes an actuating device, a pressurized fluid source, a control device and a manually operated selector device. The actuating device is coupled to the gripping mechanism and operable to apply the pulling force thereto. The pressurized fluid source is operable to supply pressurized fluid for the actuating device. The control device is coupled between the pressurized fluid source and the actuating device and is configurable between a plurality of control settings to provide a selected controlled application of pressurized fluid from the pressurized fluid source to the actuating device. The manually operated selector device is coupled to the control device and selectively operable to configure the control device to one of the control settings that will provide the selected controlled application of pressurized fluid sufficient to apply a desired pulling force on the gripping mechanism so as to transmit and apply in a sustained manner the desired pulling force on the tether independently from the tether displacement and thereby to place the tether under a desired level of sustained tension while the tether is secured proximate to the target.

In a further aspect of the present invention, a method for applying sustained tension on a tether in a treatment site includes positioning an actuating device at a fixed distance relative to a target in the treatment site, coupling a portion of the tether that extends from the treatment site with the actuating device, and applying a fluid under pressure from a pressurized fluid source to the actuating device sufficient to cause the actuating device to apply a desired tensioning force to the tether independently from the tether displacement and thereby to place the tether under a desired level of sustained tension. The method also includes securing the tether proximate to the target in the treatment site so as to retain the desired level of sustained tension on the tether in the treatment site.

BRIEF DESCRIPTION OF THE DRAWINGS

Figure 1:
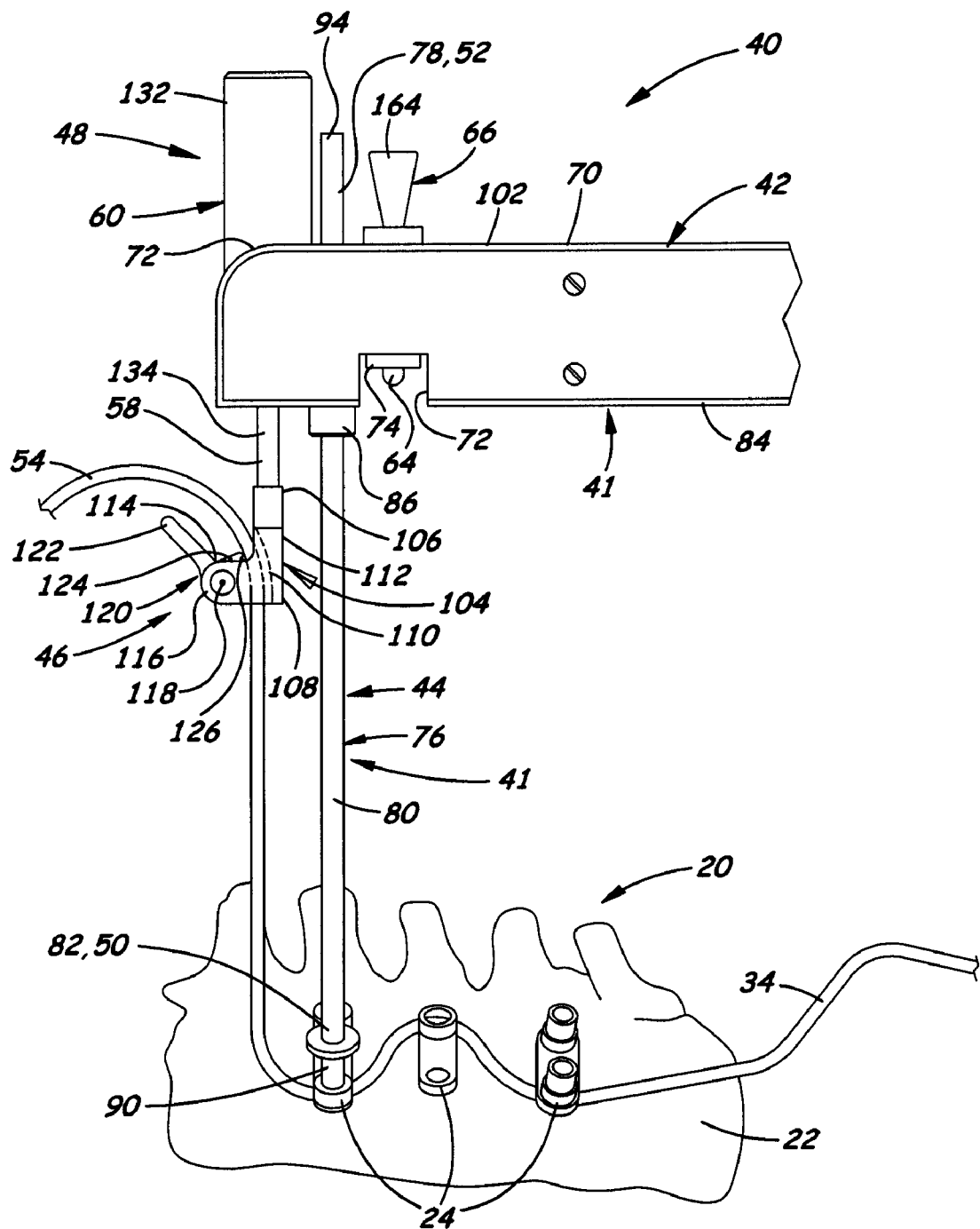

Having thus described the invention in general terms, reference will now be made to the accompanying drawings, which are not necessarily drawn to scale, and wherein:

FIG. 1 is a perspective view of a first exemplary embodiment of a tether tensioning apparatus in accordance with the present invention, showing a positioning mechanism with a distal end engaged on a target such as an implant in the treatment site and also showing a tether gripped by a gripping mechanism and a pulling force applied by a pressurized fluid actuated mechanism.

Figure 2:
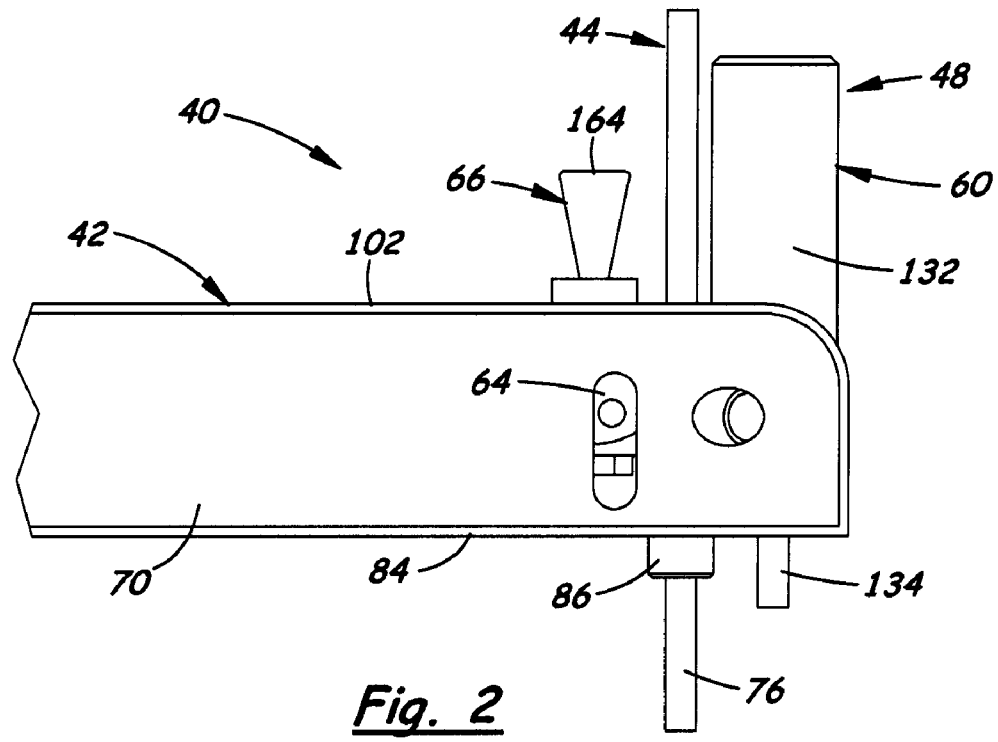

FIG. 2 is a partial side elevational view of the apparatus of FIG. 1 showing the positioning mechanism and the pressurized fluid actuated mechanism of the apparatus.

Figure 3:
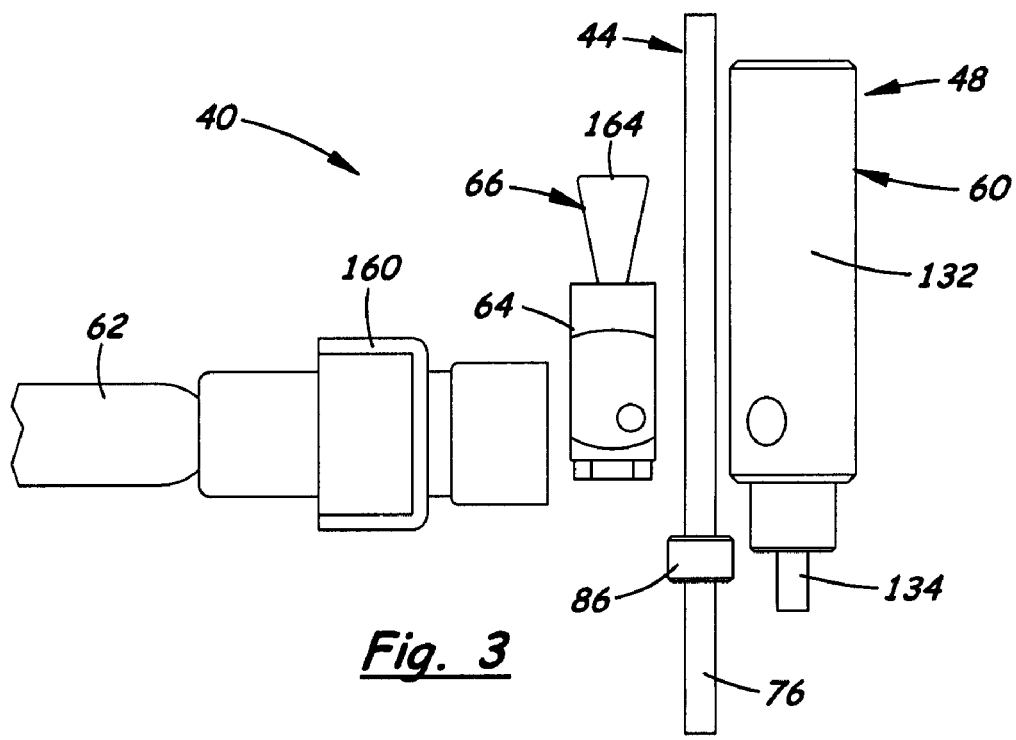

FIG. 3 is another partial side elevational view of the apparatus of FIG. 1 similar to the view of FIG. 2, but showing the positioning mechanism and components of the pressurized fluid actuated mechanism without the housing.

Figure 4:
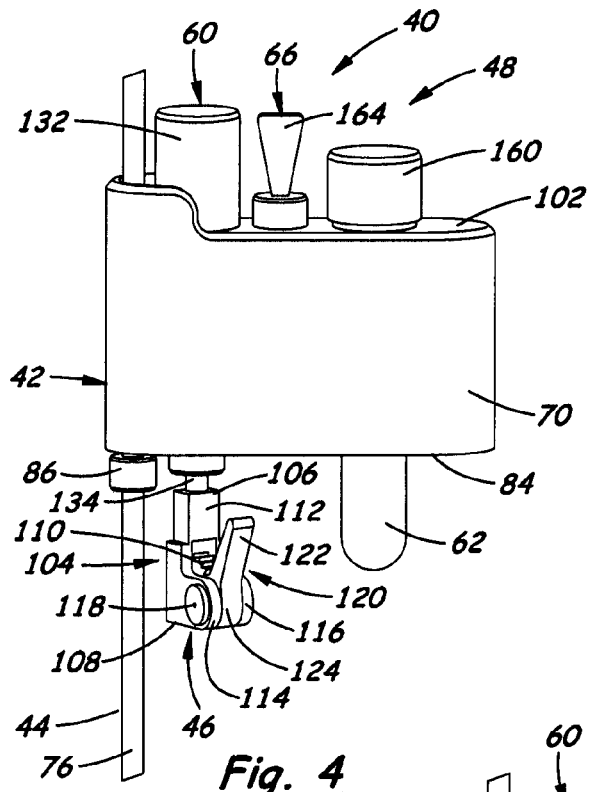

FIG. 4 is another partial side elevational view of the apparatus having an arrangement of the positioning mechanism, the gripping mechanism and the pressurized fluid actuated mechanism alternative to that of FIG. 3.

Figure 5:
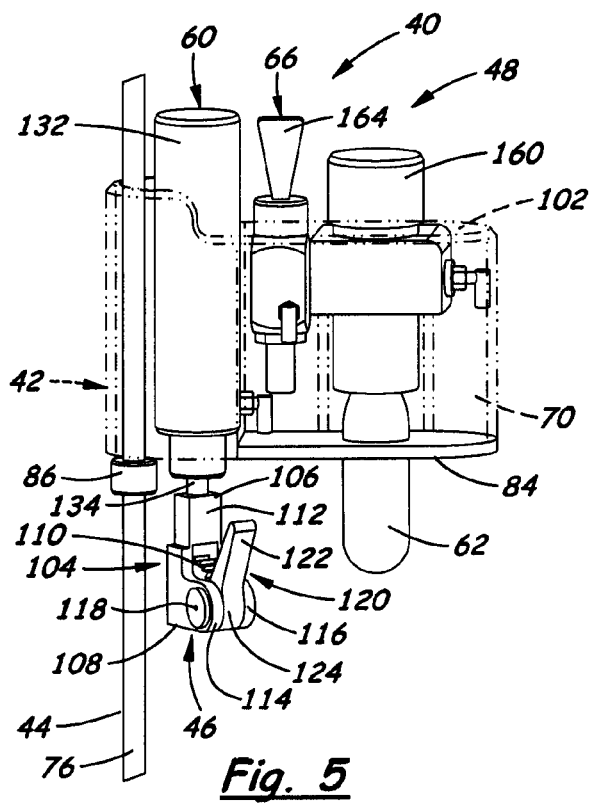

FIG. 5 is another partial side elevational view of the apparatus similar to that of FIG. 4, but showing the housing in phantom outline form.

FIG. 6 is another partial side elevational view of the apparatus having an arrangement of the positioning mechanism, the gripping mechanism and the actuator mechanism alternative to that of FIGS. 2 and 4, showing use of a pressure regulator instead of valve and also showing gripping mechanism in non-gripping position relative to the tether.

FIG. 7 is another partial side elevational view of the apparatus similar to that of FIG. 6, now showing the gripping mechanism gripping the tether.

FIG. 8 is a perspective view of a second exemplary embodiment of a tether tensioning apparatus according to the present invention, showing the gripping mechanism in a released position relative to the pressurized fluid actuated mechanism of the apparatus.

Figure 9:
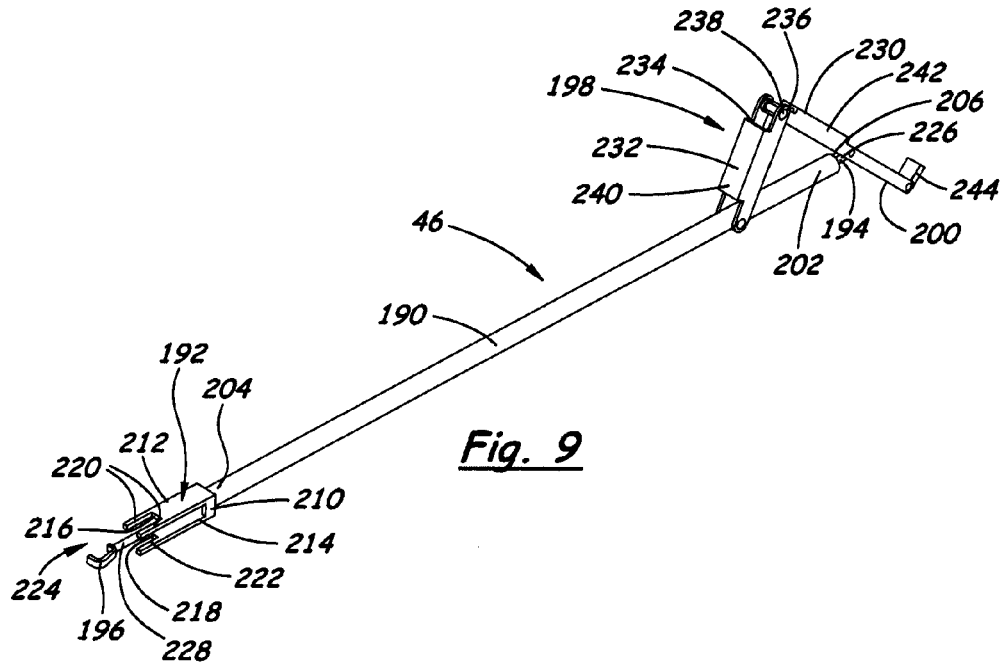

FIG. 9 is a perspective view of the gripping mechanism of the apparatus of FIG. 8, showing its articulated joint in an erected position and its end hook in a non-gripping position relative to a tether (not shown).

Figure 10:
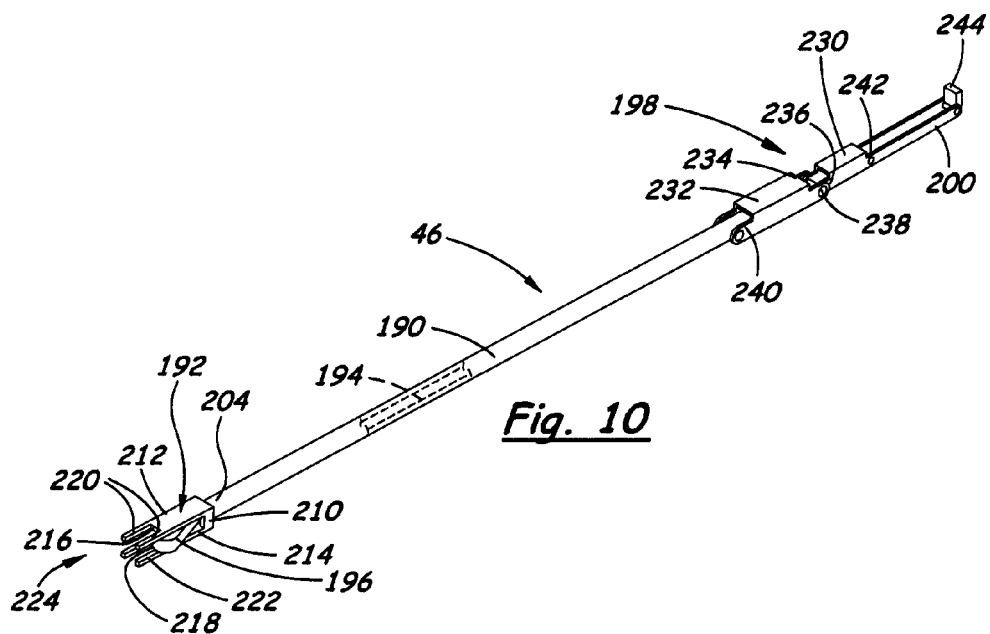

FIG. 10 is another perspective view of the gripping mechanism of the apparatus of FIG. 8 showing its articulated joint in a collapsed position and its end hook in a gripping position relative to the tether.

FIG. 11 is a perspective view of the apparatus similar to that of FIG. 8, showing the gripping mechanism with its articulated joint in the collapsed position of FIG. 10, but with the gripping mechanism not connected to the pressurized fluid actuated mechanism.

FIG. 12 is another perspective view of the apparatus similar to that of FIG. 11, but showing a pulling force applied on the gripping mechanism by the pressurized fluid actuated mechanism such that gripping mechanism is moved toward the housing and away from the treatment site (not shown).

Figure 13:
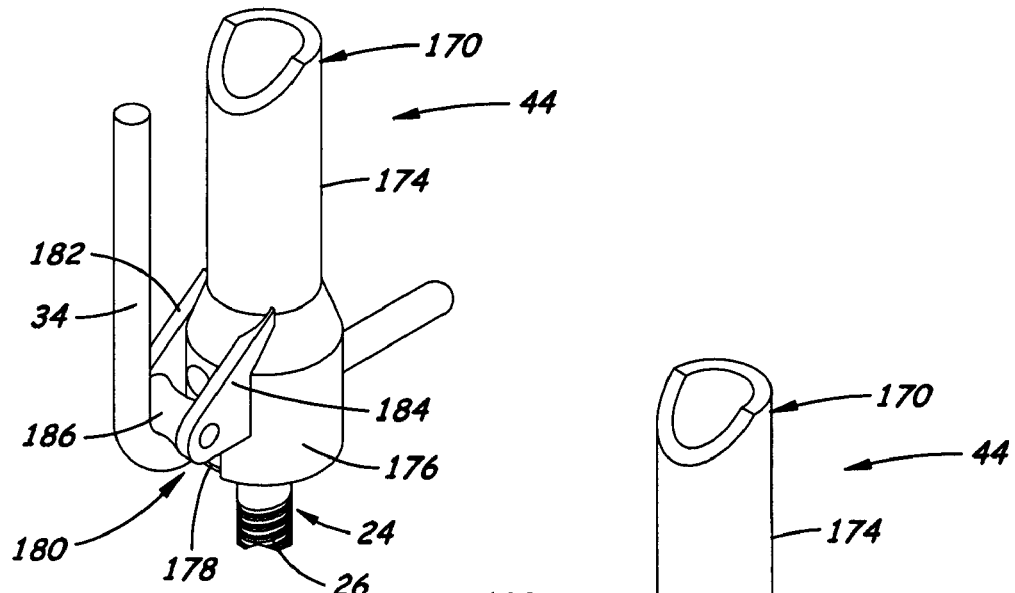

FIG. 13 is an enlarged partial perspective view of a distal end portion of a positioning mechanism such as may be used on the embodiment of the apparatus of FIG. 8 as well as other embodiments of the apparatus, showing the distal end of the positioning mechanism engaged with an implant in the treatment site having a tether running through the implant.

Figure 14A:
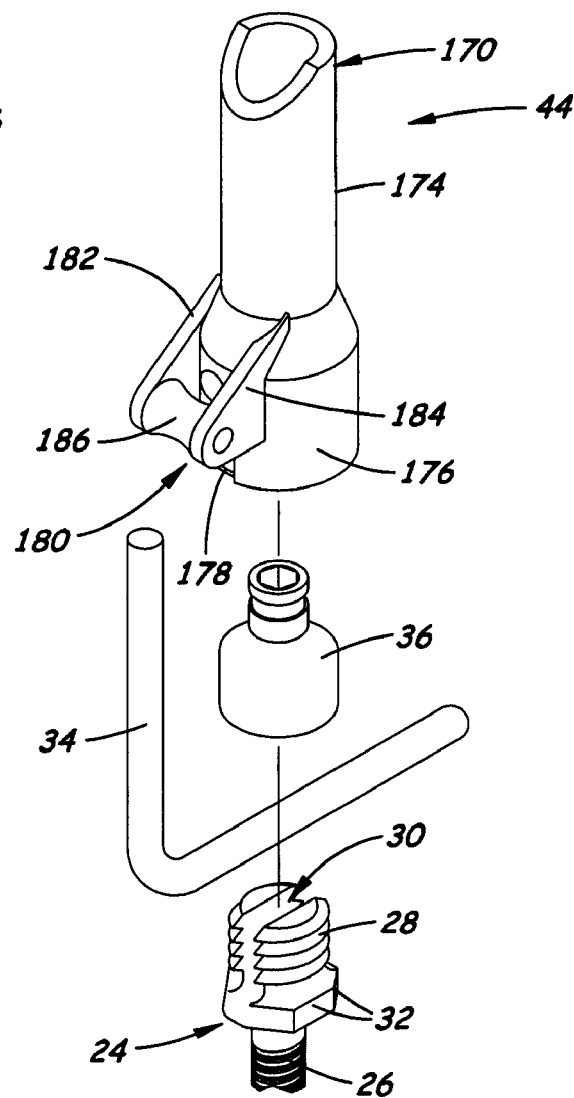

FIG. 14A is an exploded perspective view of the distal end portion of the positioning mechanism shown in FIG. 13 along with the implant and tether running through the implant.

Figure 14B:
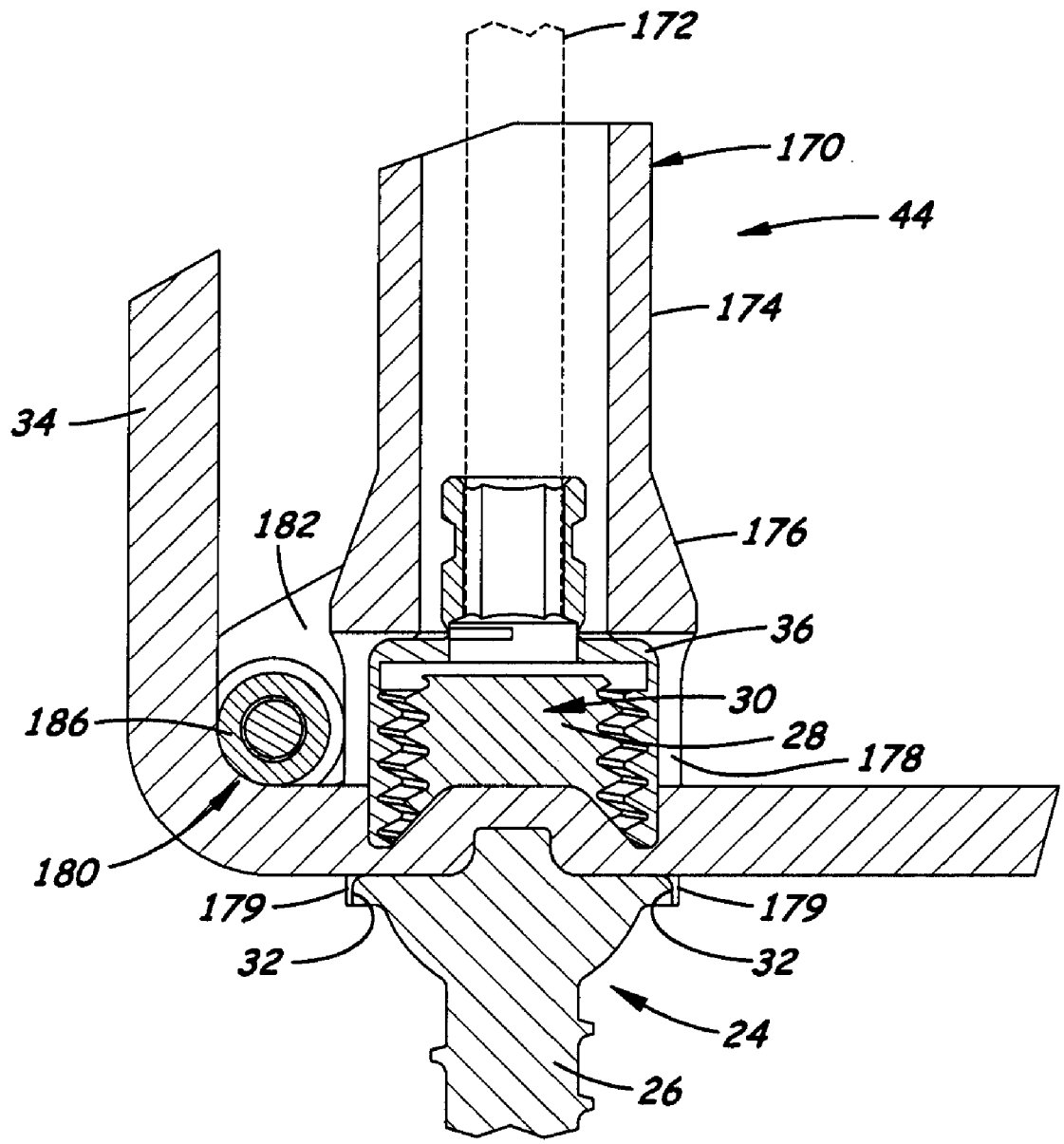

FIG. 14B is an enlarged axial sectional view taken along a central axis of the distal end portion of the positioning mechanism shown in FIG. 13.

Figure 15:
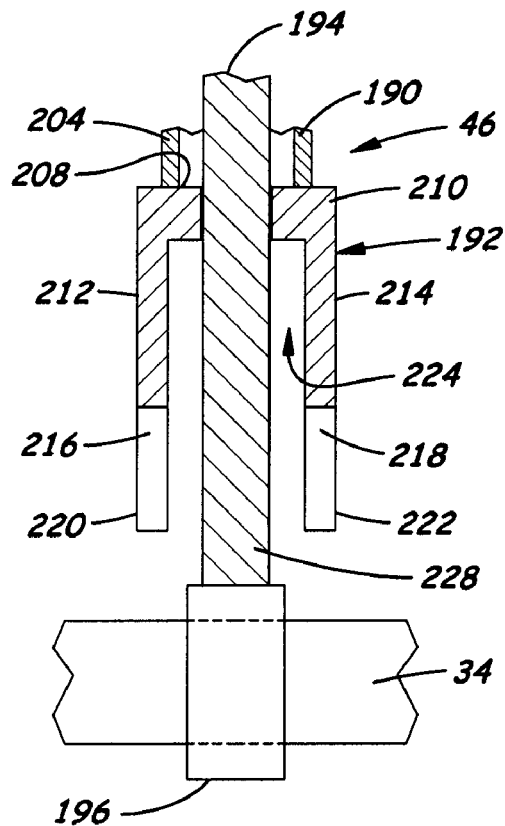

FIG. 15 is an enlarged axial sectional view taken along a central axis of the gripping mechanism in FIG. 9, showing the end hook of the gripping mechanism receiving the tether but displaced to an extended or distal position away from a guide bracket of the gripping mechanism such that the end hook does not grip the tether.

Figure 16:
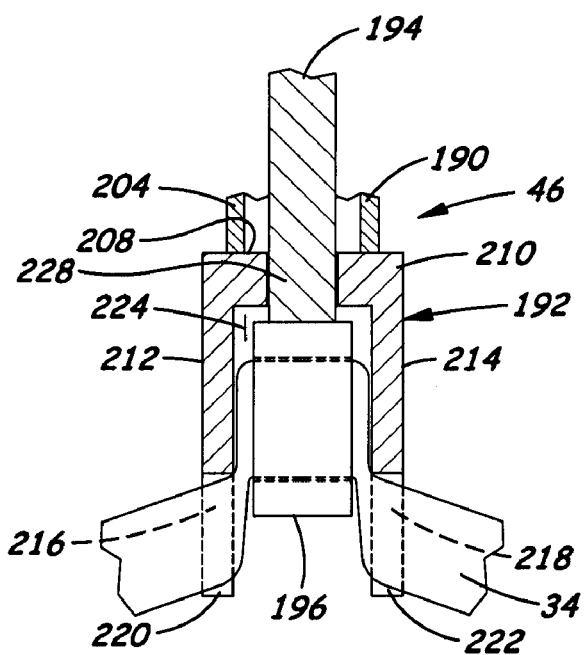

FIG. 16 is another axial sectional view similar to that of FIG. 15, but showing the end hook of the gripping mechanism displaced to a retracted or proximal position into the guide bracket such that the end hook grips the tether.

Figure 17:
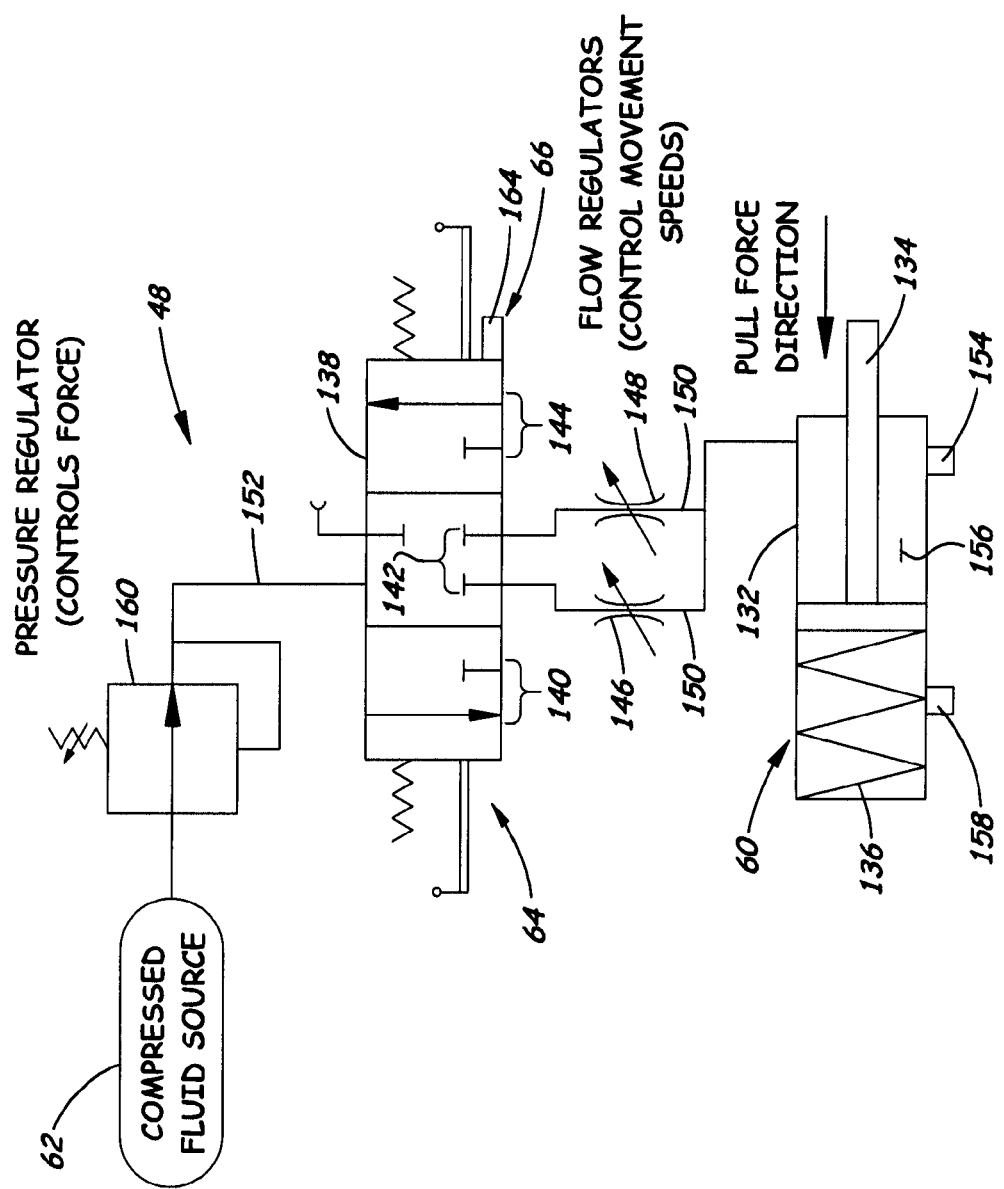

FIG. 17 is a schematic diagram of a first exemplary embodiment of components making up the pressurized fluid actuated mechanism of either of the tether tensioning apparatuses of FIGS. 1, 4 and 8.

Figure 18:
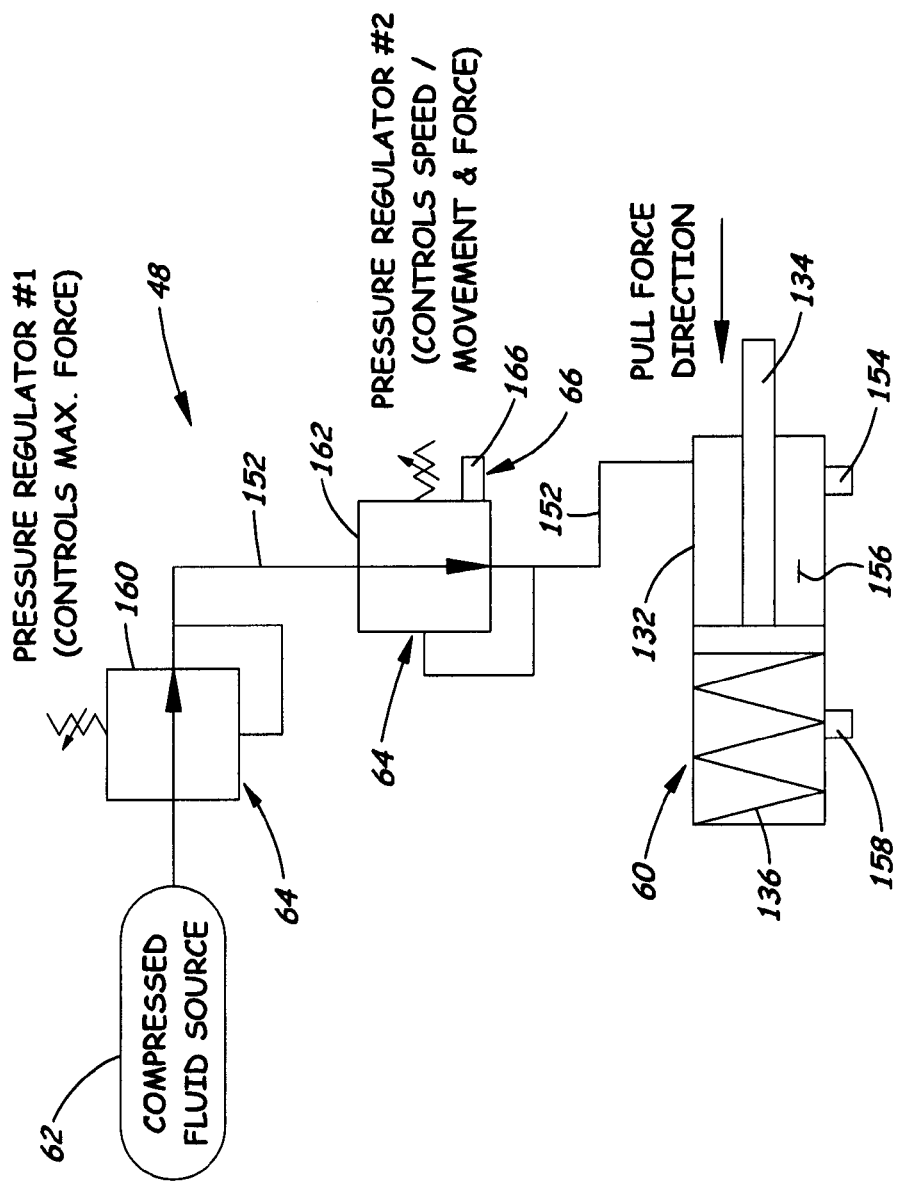

FIG. 18 is a schematic diagram of a second exemplary embodiment of components making up the pressurized fluid actuated mechanism of either of the tether tensioning apparatuses of FIGS. 6 and 7.

Figure 19:
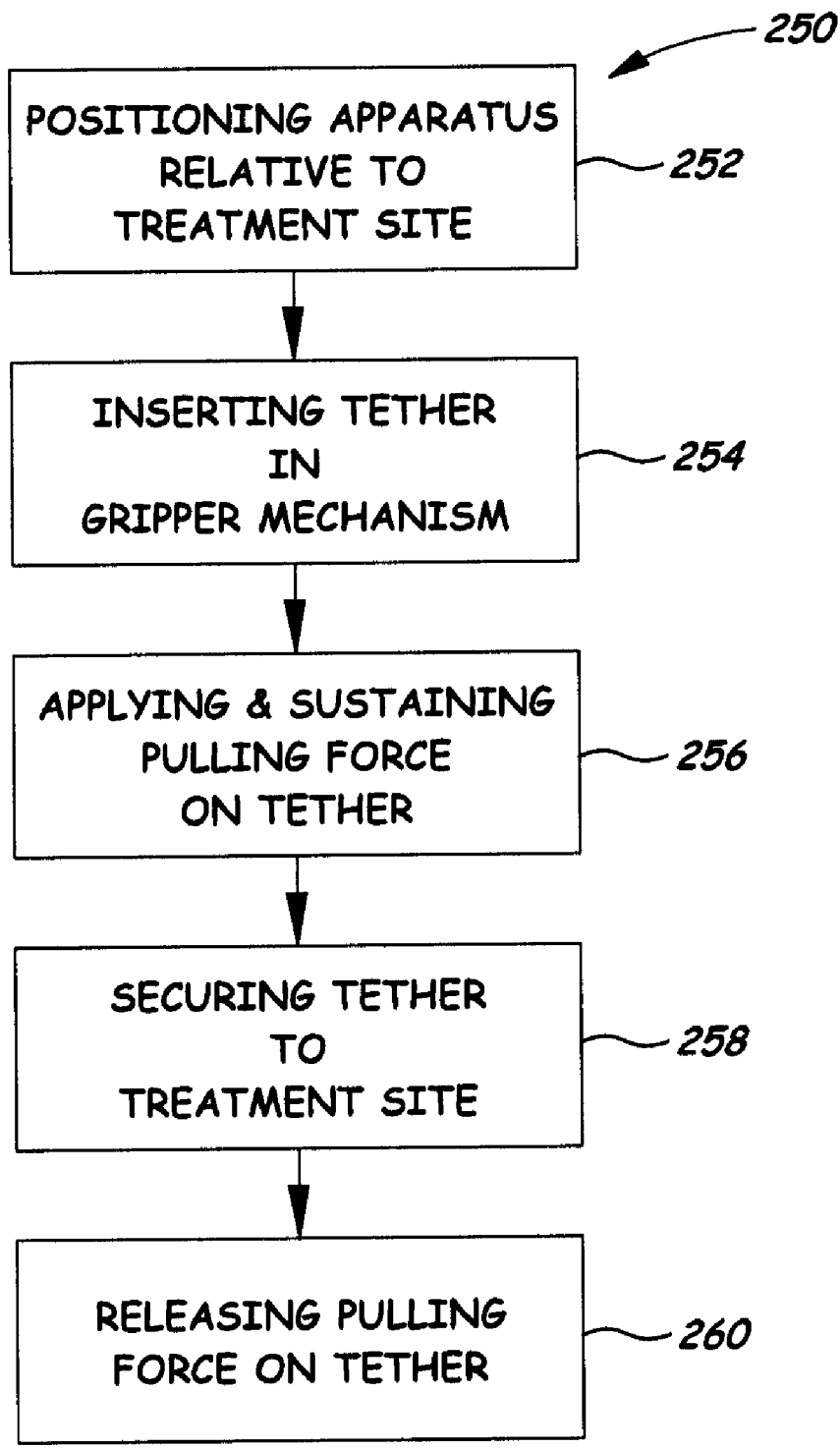

FIG. 19 is a block diagram of an exemplary embodiment of the steps making up the tether tensioning method in accordance with the present invention.

DETAILED DESCRIPTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numerals refer to like elements throughout the views. Particularly, in the following disclosure, the invention is described and illustrated in an application where the tether is tensioned and secured to an implant. However, the implant is merely one example of a type of target to which the invention can be applied. Another example is bone itself to which the tensioned tether can be secured. Therefore, it should be understood that, as reflected by the appended claims, the invention is not limited by the particular application disclosed and illustrated herein.

Referring now to FIG. 1, there is illustrated a treatment site 20 in the form of a portion of a spinal column having several vertebrae 22. Firmly attached to some of these vertebrae 22 are spinal implants 24. As best seen in FIGS. 14A and 14B, each implant 24 may have a lower externally-threaded bone screw portion 26 and an upper externally-threaded exposed head portion 28 protruding thereabove. The exposed upper head portion 28 has a transverse slot 30, open at its opposite ends and from above, through which a tether 34, or similar flexible media, may be inserted. The tether 34 may then be secured in place on the upper head portion 28 of the implant 24 by fastening a tether nut 36 thereon in order to tightly clamp and hold the tether 34 in place. The tether 34 thus positioned through two or more implants 24 can be held in tension and tightly clamped down with the tether nut 36.

Referring now to FIGS. 1 and 8, two exemplary embodiments of a tether tensioning apparatus, generally designated 40, of the present invention, are shown. In the first embodiment, shown in FIG. 1, a tether tensioning apparatus 40 is shown to operate on the treatment site 20. In the second embodiment, shown in FIG. 8, only the tether tensioning apparatus 40 is shown. In both embodiments, the tether tensioning apparatus 40 includes a positioning mechanism 41 comprised of a housing 42 and a support member 44. In both embodiments, the tether tensioning apparatus also includes a gripping mechanism 46 and a pressurized fluid actuated mechanism 48. Both embodiments are operable to grip the tether 34, apply sustained tension thereto. In one or both embodiments the fastener, such as in the form of the tether nut 36, may be applied to the implant 24 so as to secure the tether 34 in tension between two or more implants 24 in the treatment site 20.

In both embodiments, the housing 42 is positioned a fixed distance from the treatment site 20 by way of its mounting to the support member 44. The distal end 50 of the support member 44 engages a selected one of the implants 24 affixed to the treatment site 20. The selected implant 24 provides a contact surface for the distal end 50 of the support member 44 for supporting the housing 42 adjacent to the proximal end 52 of the support member 44. The support member 44 is also operable to apply the tether nut 36 to the implant 24 on the treatment site 20. The gripping mechanism 46 is situated and movable between the treatment site 20 and the housing 42. The gripping mechanism 46 is operable to grip one free end 54 of the tether 34 and to maintain that grip in a self-locking fashion when the gripped tether 34 is held in tension by the pressurized fluid actuated mechanism 48. The proximal end 56 of the gripping mechanism 46 couples with the distal end 58 of the pressurized fluid actuated mechanism 48. The gripping mechanism 46, therefore, is physically separated from the housing 42 and support member 44 and has an overall length less than the distance between the distal end 58 of the pressurized fluid actuated mechanism 48 and the treatment site 20 and a range of movement therebetween. The pressurized fluid actuated mechanism 48 produces a pulling force on the proximal end 56 of the gripping mechanism 46. The gripping mechanism 46 then transmits this force onto the gripped tether 34 to produce tension therein. The pressurized fluid actuated mechanism 48 is mounted to or integrated in the housing 42. With the housing 42 positioned at a fixed distance from the treatment site 20 by the support member 44 and the tether 34 fixedly clamped to a location on the treatment site 20 or elsewhere, the pressurized fluid actuated mechanism 48 is operable to transmit force in a sustained manner to the gripping mechanism 46, and through the gripping mechanism 46 to the tether 34 so that a desired level of tension may be selectively applied in the sustained manner to the tether 34. The tether nut 36 then may be applied by the support member 44, or with another fastening tool device (not shown). Once the tether nut 36 has been applied, the pressurized fluid actuated mechanism 48 is operable to release the pulling force from the gripping mechanism 46. One way, as shown in FIG. 1, includes using the support member 44 to tighten the tether nut 36 into place while the gripping mechanism 46 and pressurized fluid actuated mechanism 48 coact to maintain the free end 54 of the tether 34 at a desired level of tension.

In both exemplary embodiments of the apparatus 40 and also shown in FIGS. 2-8, 17 and 18, the pressurized fluid actuated mechanism 48 includes an actuating device 60, a source 62 of compressed fluid, a control device 64, and a selector device 66. The actuating device 60, which is coupled to the proximal end 56 of the gripping mechanism 46, becomes pressurized with the pressurized fluid from the pressurized fluid source 62. While the control device 64 manages the passage of the pressurized fluid to the actuating device 60, the selector device 66 couples with the control device 64 making the control device configurable to a plurality of control settings. With a force application control setting selected, the pressurized fluid from the pressurized fluid source 62 engages the actuating device 60 and thereby causes the actuating device 60 to apply a desired pulling force in a sustained manner on the proximal end 56 of the gripping mechanism 46.

Referring now to FIGS. 1-7, the first exemplary embodiments of the tether tensioning apparatus 40 is shown in greater detail. The housing 42, made from a structurally supportive material such as aluminum or steel, includes a body 70 and a plurality of cutouts 72 and compartments 74 in the body 70 allowing the different components of the tether tensioning apparatus 40 to fit within or through the body 70 of the housing 42 and to be supported with respect to each other. The support member 44 includes a shaft 76, such as in the form of a solid rod or hollow tube, having proximal, middle and distal portions 78, 80, 82 which extend at least between the treatment site 20 and a lower surface 84 of the housing body 70. The proximal portion 78 of the shaft 76 has a collar 86 that underlies the lower surface 84 of the body 70 so as to thereby position the housing 42 a fixed distance from a given implant 24 in the treatment site 20. The distal portion 82 of the shaft 76 includes a socketed end portion 90 which seats at the treatment site 20 upon the given implant 24. The shaft 76 thus provides a standoff support effect between the treatment site 20 and the housing 42 with the various components affixed thereto. The proximal portion 78 of the shaft 76 extends above an upper surface 92 of the body 70 of the housing 42 exposing a detent 94. A separate tool (not shown), such as a torque limited ratchet, a wrench, or a handle, can engage the detent 94 so as to enable assisted rotation or turning of the shaft 76. When the detent 94 becomes engaged and rotated or a torque otherwise becomes applied to the proximal end 78 of the shaft 76, the shaft 76 rotates relative to the housing 42 and will tighten or loosen the tether nut 36. Also, if the tether 34 is positioned through the implant 24 to which the tether nut 36 is threaded, the tether 34 will be clamped down to or loosened from the implant 24 as the nut 36 becomes tightened or loosened, respectively.

As shown in FIGS. 4-7, the gripping mechanism 46 of the first exemplary embodiment of the apparatus 40 includes a mounting bracket 104 having proximal and distal end portions 106, 108, a passageway 110 through the distal end portion 108 so that the tether 34 may be positioned therethrough, and a connector 112 at the proximal end portion 106 that couples the gripping mechanism 46 to the actuating device 60 of the pressurized fluid actuated mechanism 48. The gripping mechanism 46 also includes left and right mounting ears 114, 116, located at the distal end portion 108 of the mounting bracket 104 and which define a pivot axis 118, and a gripping device 120 disposed between the mounting ears 114, 116. The mounting ears 114, 116 are spaced apart from each other and aligned with the passageway 110. The gripping device 120 is mounted between the mounting ears 114, 116 for undergoing pivotal movement about the pivot axis 118 and is in communication with the passageway 110. The gripping device 120 has a graspable lever 122 and a clamping member 124 integrally connected therewith and in the form of an eccentrically mounted cam defining a row of teeth 126. Initially, the clamping member 124 is rotatably and manually moved by a user about the mounting ear pivot axis 118 by using the lever 122 which allows the gripping device 120 to be placed in gripping and releasing (or non-gripping) positions, shown in FIGS. 7 and 6 respectively, relative to the tether 34 positioned in the passageway 110. Once the clamping member 124 of the gripping device 120 grips a portion of the tether 34 positioned in the passageway 110 and the actuating device 60 applies a pulling force on the gripping mechanism 46, the clamping member 124 becomes self-locking. The self-locking effect occurs when the applied pulling force on the gripping mechanism 46 from the actuating mechanism 48, combined with the standoff support effect from the support member 44 and housing 42 of the positioning mechanism 41, causes the tether 34 to translate slightly and causes the clamping member 124, due to its eccentrically mounted cam form, to rotate slightly thereby increasing the teethed grip on the tether 34.

Referring to FIGS. 1-5 and 17, the pressurized fluid actuated mechanism 48 of the first exemplary embodiment of the apparatus 40, as mentioned earlier, includes the pressurized fluid source 62 that may be of various forms, such as a replaceable cartridge of liquid or compressed gas, a compressed gas pipeline source, a hydraulic pump or accumulator, etc. The actuating device 60 providing linearly actuating motion to the gripping mechanism 46 may also be of various forms with changeable volumes, such as pneumatic or hydraulic cylinders, actuating bellows, a rotating pneumatic or hydraulic cylinder with winching drum, etc. In the exemplary form seen in FIG. 17, the actuating device 60 includes a casing or cylinder 132, a piston rod 134 slidably movable in the cylinder 132 between extended and retracted positions and biased by a spring 136. The control device 64 that manages the passage of fluid for the pressurized fluid actuated mechanism 48 includes a control valve 138 that is shiftable or slidable between a plurality of positions, as shown in FIG. 17, including a first position 140 for introducing pressure, a second position 142 for halting introduction of pressure, and a third position 144 for relieving pressure. As shown in FIGS. 1-5, each of the respective positions is selectable by way of the selector device 66 coupled to the control valve 138. The control device 64 also may use flow regulators 146, 148 positioned along the pressure lines 150 between the control valve 138 and the cylinder 132 to control the movement speed of the actuating device 60. A pressure gage 154 may engage the interior 156 of the cylinder 132 to detect the pressure level applied to the piston rod 134. It should be noted that the gage 154 may be placed at a suitable alternative location, such as along the pressurized lines 150 leading between the control valve 138 and the cylinder 132. Additionally, a full retraction sensor 158 can be coupled to the actuating device 60 in order to indicate to the user that the actuating device 60 has reached a fully retracted position and that, for example, the tether 34 might not be tensioned correctly or that it may be necessary to loosen the tether 34 to repeat the tensioning operation.

Also in the pressurized fluid actuated mechanism 48 of the first exemplary embodiment of the apparatus 40, a first pressure regulator 160 is positioned along a pressure line 152 between the pressurized fluid source 62 and the actuating device 60 to regulate and keep consistent or sustain the pressure of the pressurized fluid transmitted to the actuating device 60. In FIGS. 1-3, 6, and 7, the first pressure regulator 160 is integrated into the housing 42 lying transversely adjacent to the support member 44 and pressurized fluid actuated mechanism 48. A second pressure regulator 162 may also be used in sequence with a first pressure regulator 160. In this dual-regulator configuration, as shown in FIGS. 6, 7, and 18, the first pressure regulator 160 reduces the pressure of the pressurized fluid source 62, such as from about 800 psi as contained in a $CO_2$ cartridge, to a maximum level suitable for the other tensioning apparatus components, such as about 250 psi, or for the biologically maximal pressure limits associated with the treatment site 20. The second pressure regulator 162 then substitutes for the control valve 138 of the hereinbefore described control device 64 by controlling the pressure level transmitted to the actuating device 60 in a selectable range from zero to a desirable value below the maximal pressure by visually assessing vertebrae movement (deformity correction degree) at the treatment site. This second regulator 162 includes a manual selector device 164 coupled thereto having the form of a turnable knob 166 so as to allow for the range of pressure levels. The second pressure regulator 162 and selector device 164 may also be used without the first pressure regulator 160 to step down the pressure level and without the control valve 138. Another form of the pressurized fluid actuated mechanism 48 is shown in FIGS. 4 and 5. Here, the first pressure regulator 160 and pressurized fluid source 62 of the pressurized fluid actuated mechanism 48 lies parallel with the support member 44, each at respective outside positions through the housing 42 while the gripping mechanism 46 lies adjacently below the lower surface 84 of the body 70 of the housing 42 and parallel and between the regulator 160 and support member 44.

Referring now to FIGS. 8-16, the second exemplary embodiment of the tether tensioning apparatus 40 is shown in greater detail. The housing 42 is smaller and more compact than the first embodiment, having the first regulator 160 and pressurized fluid source 62 extending transversely from the first and gripping mechanism s 44, 46 and forming a handle 168. The housing 42 of the second embodiment also supports or integrates the different components of the tether tensioning apparatus 40 at their desired positions with respect to each other. The support member 44 of the second embodiment includes a shaft 170 in the form of a hollow tube. A nut driver 172 in the form of an elongated rod disposed in the hollow shaft 170. The distal portion 174 of the shaft 170 includes a socketed end portion 176 having opposed slots 178 formed in opposite sides thereof allowing clearance for the tether 34 to be positioned therethrough. The socketed end portion 176 allows the shaft 170 to mate with or seat upon the one implant 24 or other implant components situated at the treatment site 20 so as to provide standoff support between the treatment site 20 and the housing 42, and therewith the gripping mechanism 46 and pressurized fluid actuated mechanism 48. The nut driver 172 may also be rotatably and slidably mounted and movable within the shaft 170 so as to enable tightening and loosening of the tether nut 36 within the space enclosed by the socketed end portion 176 of the shaft 170. If the tether 34 is positioned through the opposed slots 178 and the transverse slot 30 in the upper head portion 28 of the implant 24 on which the tether nut 36 is threaded, the tether 34 will be clamped down to or loosened from the nut 36 as the nut becomes tightened or loosened, respectively. The distal portion 174 of the shaft 170 also includes a roller device 180, as shown in FIGS. 13, 14A and 14B, having two spaced apart brackets 182, 184 affixed to a side of the shaft 170 and a roller 186 disposed between and rotatably mounted by the brackets 182, 184. The roller 186 guides the tether 34 on an obtuse path through the opposed slots 178 of the socketed end portion 174 of the shaft 170 and thereby prevents substantial forced contact with the nut 36 as it becomes tightened down on the tether 34 during tightening application by the nut driver 172. The reduced contact force prevents the tether 34 from deleterious abrasion and fraying that may occur through all but the final turns clamping the tether 34 in place. The socketed end portion 174 of the shaft 170 has internal detents (or flat areas) 179 shaped to mate with corresponding external detents (or flat areas) 32 on the implant 24 so as to provide a counter torque to the torque applied by the nut driver 172 to the tether nut 36 which prevents rotation of the implant 24 when the tether nut 36 is turned.

The gripping mechanism 46 of the second exemplary embodiment of the apparatus 40 basically includes a support tube 190, a guide bracket 192, an elongated rod 194, an end hook 196, an articulated joint 198, and a connector bracket 200. The support tube 190 has opposite proximal and distal end portions 202, 204, each with respective open ends 206, 208. The guide bracket 192 attaches to and extends axially from the distal end portion 204 of the support tube 190. The guide bracket 192 attaches at a middle portion 210 thereof to the distal end 208 of the support tube 190. The guide bracket 192 is of bifurcated shape such that two opposite side portions 212, 214 of the guide bracket 192 extend from the middle portion 210 thereof axially with respect to the support tube 190. The opposite side portions 212, 214 have respective end recesses 216, 218 defining two spaced apart U-shaped pairs of opposite end legs 220, 222 and a passageway 224 extending between the opposite side portions 212, 214 through the guide bracket 192 between each pair of opposite legs 220, 222 thereof, from one end recess 216 to the other 218, and transversely aligned with the open end 208 of the distal end portion 204 of the support tube 190.

The rod 194 extends through the support tube 190 and is greater in length than the support tube 190. The additional length allows the respective opposite proximal and distal end portions 226, 228 of the rod 194 to extend from the opposite open ends 206, 208 of the support tube 190 with the distal end portion 228 of the rod 194 also extending through the passageway 224 of and beyond the guide bracket 192, with the support tube 190 being axially movable relative to the rod 194. The hook 196 attaches to the distal end portion 228 of the rod 194 and aligns with the passageway 224 of the guide bracket 192. The hook 196 is disposed to slidably move beyond the guide bracket 192 and configured to fit partially around the tether 34. To accomplish this, the support tube 190 moves axially relative to the rod 194 and away from the treatment site 20 so as to dispose the hook 196 at a distal position, as seen in FIGS. 9 and 15, outside of the passageway 224 of the guide bracket 192 and beyond the guide bracket 192 so that the tether 34 can be placed in a non-gripping relation with the hook 196. The tether 34 moves into a gripping relation with the hook 196 as the support tube 190 moves axially relative to the rod 194 and toward the treatment site 20 disposing the hook 196 at a proximal position in the passageway 224 of guide bracket 192, as seen in FIGS. 8, 10, and 16. As the hook 196 moves into the passageway 224 and reaches the distal open end 208 of the support tube 190, the end recesses 216, 218 and opposite end legs 220, 222 of the guide bracket 192 block movement of the tether 34 away from the non-gripping relation with the hook 196, and the tether 34 cinches between each opposite side portion 212, 214 of the guide bracket 192 and becomes deformed into a gripping relation with the hook 196 within the passageway 224 of the guide bracket 192.

The articulated joint 198 is formed by a proximal lever 230 and a distal lever 232, each of a generally U-shaped cross-section and having adjacent portions 234, 236, pivotally connected together by rivets 238 and having remote portions 240, 242 respectively pivotally connected to proximal end portions 226, 202 of the rod 194 and support tube 190 such that the proximal and distal levers 230, 232 are pivotally movable between an erected position and a collapsed position. The erected position, as seen in FIG. 9, has the proximal and distal levers 230, 232 articulated relative to one another away from the rod 194 and support tube 190 into an angular relationship with one another. The support tube 190 is axially moved relative to the rod 194 and away from the treatment site 20 placing the hook 196 in the distal position outside the passageway 224 of the guide bracket 192 so the tether 34 can be placed in a non-gripping relation with the hook 196. The collapsed position, as seen in FIG. 10, has the proximal and distal levers 230, 232 aligned with one another lying along and generally parallel to and nested with the proximal end portions 226, 202 of the rod 194 and support tube 190. The support tube 190 is axially moved relative to the rod 194 and toward the treatment site 20 placing the hook 196 in proximal position within the passageway 224 of the guide bracket 192 with the tether 34 deformed into a gripping relation by the hook 196 and guide bracket 192. The connector bracket 200 is an axial extension of the proximal lever 230 beyond the pivot connection of the proximal lever 230 and proximal end portion 226 of the rod 194 to a proximal end 244 of the connector bracket 200 that flexibly couples to a distal end 246 of the actuating device 60 of the pressurized fluid actuated mechanism 48. This flexible connection 248 between connector bracket 200 and actuating device 60 accommodates movement of the articulated joint 198 between its erected and collapsed positions.

An exemplary embodiment of the basic steps of the method in accordance with the present invention for applying tension on the tether 34, employing the tether tensioning apparatus 40, is shown in the block diagram 250 of FIG. 19. As per block 252, the actuating device 60, by using the positioning mechanism 41, is positioned at a fixed distance relative to the treatment site 20. As per block 254, a portion of the tether 34 to be pre-tensioned extending from the treatment site 20 is then coupled to the actuating device 60 by being inserted into the gripping mechanism 46 which is operable to grip the portion of the tether 34. As per block 256, a controlled and sustained level of pressurized fluid is then applied, as per operation of the components described hereinbefore of the pressurized fluid actuated mechanism 48 and shown in FIGS. 17 and 18, to the actuating device 60 so as to cause the actuating device 60 to apply and sustain a desired pulling force on the gripping mechanism 46. The force on the gripping mechanism 46 is directed away from the treatment site 20 so as to transmit and apply in the sustained manner the desired pulling force on the tether 34 independently from the tether displacement and sufficient to cause a desired level of tensioning of the tether 34 in the treatment site 20. As per block 258, the tether 34 is then secured to the treatment site 20 with the desired level of tension such as by securing the fastener or nut 36 over it and onto a given one implant 24 in the treatment site 20. As per block 260, the pulling force applied on the tether 34 by the gripping mechanism 46 is then released, as per operation of the components described hereinbefore and shown in FIGS. 17 and 18, when the fastener has been applied to and the tether 34 secured to the implant 24.

The term "sustained tension" as used hereinbefore will be understood to mean a persistent dynamic load imposed on the tether without manipulating the selector device in response to the tether displacement. Also, the term "pressurized fluid" as used hereinbefore will be understood to refer to pneumatic or hydraulic fluids, for example, of a pressure range between about 100 KPa to 1000 KPa. The load range may be between about 50 to 500 Newton.

The foregoing description of several embodiments of the invention has been presented for purposes of illustration. It is not intended to be exhaustive or to limit the invention to the precise forms disclosed, and obviously many modifications and variations are possible in light of the above teaching. It is intended that the scope of the invention be defined by the claims appended hereto.

What is claimed is:

1. An apparatus for applying sustained tension on a tether in a treatment site, said apparatus comprising:

a positioning mechanism having a distal portion operable to engage a target at the treatment site proximate to where the tether is to be secured, said positioning mechanism also having a proximal portion displaced from said distal portion;

a gripping mechanism operable to grip the tether and maintain the grip of the tether when the tether is held in tension, the gripping mechanism including a support tube having opposite open distal and proximal end portions and a guide bracket mounted at said distal end portion;

a rod extending through said support tube and having proximal and distal end portions beyond said opposite open distal and proximal end portions of said support tube such that said rod and support tube can undergo axial movement in opposite directions relative to one another, said rod having a tether engaging member mounted to said distal end portion of said rod such that said tether engaging member and guide bracket on said support tube undergo relative movement between tether non-gripping and tether gripping relations with one another upon said support tube and said rod undergoing said axial movement in opposite directions relative to one another; and an articulated joint having proximal and distal levers with adjacent ends pivotally connected to each other and remote ends respectively pivotally connected to said proximal end portions of said support tube and rod such that upon movement of said articulated joint between erected and collapsed positions respectively away from and along said support tube and rod said support tube and rod undergo said axial movement in opposite directions relative to one another and said tether gripping member and guide bracket undergo relative movement between tether non-gripping and tether gripping relations with one another; and a pressurized fluid actuated mechanism supported by said proximal portion of said positioning mechanism at a position a fixed distance relative to the treatment site, said pressurized fluid actuated mechanism being operable to apply a controlled tensioning force via said gripping mechanism to the tether independently from the tether displacement and thereby to place the tether under a desired level of sustained tension.

2. The apparatus of claim 1 wherein said positioning mechanism includes a support member defining said distal portion of said positioning mechanism which seats at the treatment site on the target and also defining said proximal portion of said positioning mechanism which is displaced from said distal portion.

3. The apparatus of claim 2 wherein said positioning mechanism also includes a housing mounted to said proximal portion of said support member and supporting said pressurized fluid actuated mechanism at said position said fixed distance from the target such that said support member provides a standoff support effect between the treatment site and said pressurized fluid actuated mechanism.

4. The apparatus of claim 2 wherein said support member includes a driver rod having a distal end portion adapted to apply a fastener on an implant to secure the tether thereto by turning said driver rod.

5. The apparatus of claim 4 wherein said distal portion of said support member is adapted to seat on the implant so as to provide a counter torque to the turning of said driver rod to prevent turning of the implant.

6. The apparatus of claim 5 wherein said support member includes a tubular shaft surrounding said driver rod and having a distal end portion adapted to seat on the implant so as to provide a counter torque to the turning of said driver rod to prevent turning of the implant.

7. The apparatus of claim 1 wherein said gripping mechanism further includes a connector connected to said articulated joint and coupled to said pressurized fluid actuated mechanism such that when said articulated joint is at said collapsed position said support tube and rod of said gripping mechanism are movable together away from the treatment site to apply the pulling force on the tether gripped by said tether engaging member and guide bracket to tension the tether.

8. The apparatus of claim 1 wherein said pressurized fluid actuated mechanism includes an actuating device coupled to said gripping mechanism and operable to apply the pulling force thereto.

9. The apparatus of claim 8 wherein said pressurized fluid actuated mechanism further includes a pressurized fluid source operable to supply pressurized fluid pressure for said actuating device.

10. The apparatus of claim 9 wherein said pressurized fluid actuated mechanism further includes a control device coupled between said pressurized fluid source and said actuating device and being configurable between a plurality of control settings to provide a selected controlled application of pressurized fluid from said pressurized fluid source to said actuating device.

11. The apparatus of claim 10 wherein said pressurized fluid actuated mechanism further includes a manually operable selector device coupled to said control device and selectively operable to configure said control device to one of said control settings that will provide the selected controlled application of pressurized fluid pressure sufficient to apply the desired pulling force on said gripping mechanism directed away from the treatment site so as to transmit and apply in the sustained manner the desired pulling force on the tether and thereby to place the tether under the desired level of tension while the tether is secured proximate to the target, and to release said desired pulling force on the tether after the tether is secured proximate to the target.

12. A method for applying sustained tension on a tether in a treatment site, said method comprising the apparatus of claim 1 positioning the actuated mechanism at a fixed distance relative to the target in the treatment site;

coupling a portion of the tether that extends from the treatment site with the actuated mechanism; and applying a fluid under pressure from a pressurized fluid source to the actuated mechanism actuating device sufficient to cause the actuated mechanism to apply a desired tensioning force to the tether independently from the tether displacement and thereby to place the tether under the desired level of sustained tension.

13. The method of claim 12 wherein said desired tensioning force is obtained by selectively shifting a control valve between fluid introducing from the source with controlled pressure, fluid introduction halting, and fluid pressure relieving positions.

14. The method of claim 12 wherein said desired tensioning force is obtained by introducing fluid from the pressurized fluid source by adjusting a pressure regulator to a desired pressure level with a range of pressure levels.

15. The method of claim 12 further comprising:

securing the tether proximate to the target in the treatment site so as to retain the desired level of tension on the tether in the treatment site.

* * * * *